United States Patent [19]

Neueder

[11] Patent Number: 4,590,420
[45] Date of Patent: May 20, 1986

[54] APPARATUS FOR TESTING PLASTIC PROFILES BY A MAGNETICALLY SUSPENDED PROBE

[76] Inventor: F. H. Neueder, Amselstrasse 9, D-8443 Furth, Fed. Rep. of Germany

[21] Appl. No.: 564,243

[22] Filed: Dec. 21, 1983

[30] Foreign Application Priority Data

Dec. 23, 1982 [DE] Fed. Rep. of Germany ....... 3247852

[51] Int. Cl.$^4$ ..................... G01R 31/02; G01R 31/06; B61B 13/00
[52] U.S. Cl. ........................................ 324/54; 104/154
[58] Field of Search ............................ 264/40.1, 40.2; 425/140, 141; 104/154, 155, 165; 324/51, 54, 61 P, 65 P

[56] References Cited

U.S. PATENT DOCUMENTS

| | | | |
|---|---|---|---|
| 3,710,241 | 1/1973 | Dineen | 324/54 |
| 3,760,245 | 9/1973 | Halvorsen | 104/165 |
| 3,882,791 | 5/1975 | Youngscap | 104/154 |
| 4,457,423 | 7/1984 | Stoll | 104/154 |

FOREIGN PATENT DOCUMENTS 0047597 3/1982 European Pat. Off. ........... 264/40.2

Primary Examiner—Reinhard J. Eisenzopf
Assistant Examiner—Jose M. Solis
Attorney, Agent, or Firm—Kane, Dalsimer, Kane, Sullivan and Kurucz

[57] ABSTRACT

The invention proposes apparatus for testing plastic profiles or sections, particularly extruded polyethylene tubes which have been cross-linked by radiation, although the application of the invention is not restricted to that field. An electrode at a high potential and a grounded electrode are provided and surround the moving plastic section. A probe consisting preferably of a metal braid is disposed inside the profile or section adjacent to the apparatus and is preferably magnetically held and is not directly conductively grounded to the outside. Defects such as electron punctures in the wall of the plastic profile or section are detected by the breakdowns which are effected at the locations of said defects. It will be understood that the apparatus proposed by the invention can also be used to detect the location of other defects, such as contraction holes, inclusions, bubbles etc., and to deliver control signals to suitable devices for marking, rejecting etc.

10 Claims, 1 Drawing Figure

U.S. Patent
May 20, 1986
4,590,420
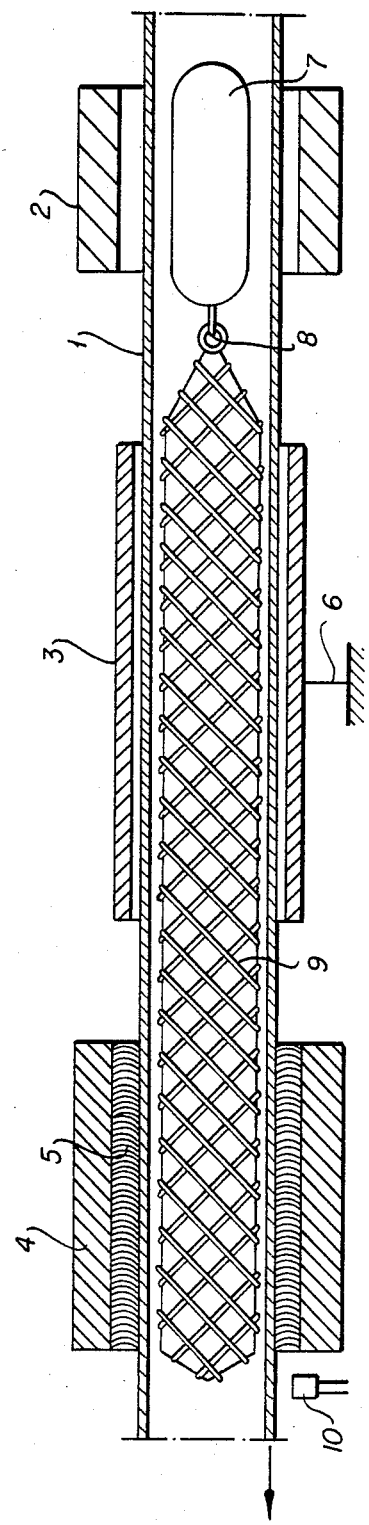

APPARATUS FOR TESTING PLASTIC PROFILES BY A MAGNETICALLY SUSPENDED PROBE

This invention relates to apparatus for testing plastic profiles or sections, particularly for testing cross-linked tubes or the like.

It is known that contraction cavities and inclusions may form during the extrusion of plastic profiles or sections and that holes may form in the wall of the profile or section during its subsequent processing, e.g., the cross-linking of polyethylene.

Particularly during the radiant cross-linking of plastic profiles or sections, profile or section walls having a thickness of some millimeters may be punctured by bombarding electrons with formation of passages which are not straight but may be entirely irregular. It has been attempted to detect such holes in that portions of the profile or section were submerged in water and subjected to air pressure so that the rising air bubbles permitted a visual detection of the locations of the puncture and the damaged portion could then be rejected. But that test cannot be used to detect other defects, such as contraction cavities or inclusions. And even the locations of the above-mentioned holes, which in a cross-linked polyethylene profile or section may consist of puncture passages having a width of about 1/10 mm, can be detected only with great restriction by said compressed-air tests conducted under water. For instance, when relatively large tube sections, particularly banks of thin tubes, are placed into a water tank and supplied with compressed air, any puncture passage existing in unintended bends of the tube may be sealed by such bend so that no air bubbles can rise from such passages. For this reason the compressed-air test is conducted in two modes. In the first mode a profile or section, e.g., a tube, is pulled through a water bath while the profile or section is pressurized. In the second mode, completely coiled tube banks in lengths of, e.g., 120, 200 or more meters are pressurized under water. Nevertheless, puncture resulting from cross-linking by radiation and penetrating the wall of the profile or section along a zig-zag line rather than a straight line may not be detected because the entrance or exit funnels or the passages in the material may be closed under the action of the air pressure or by the curvature of the wound tube banks so that air bubbles cannot escape. (Air bubbles may also collect in cavities existing in the tube bank and in that case may not escape during the test). For this reason the material amy contain undetected defects, which constitute an intolerable element of uncertainty.

In other extrusion processes the material is cross-linked, e.g., by a chemical process in which additives, such as peroxides or other substances, are added to the starting material before or during the extruding operation. It is known that the quality of plastic profiles or sections made by that process can be tested in that the locations of contraction cavities or other defects in the profile or section wall are detected by means of a high-voltage testing device and a probe contained in the tube. At the location of a defect, there will be a breakdown from the high-voltage testing device to the probe, which is disposed inside the profile or section and directly externally grounded.

The testing methods described hereinbefore cannot be used to test plastic profiles or sections which have been cross-linked by radiation. The plastic profiles or sections, which mainly consist of tubes, are usually coiled in lengths of about 3000, 4000 and more meters on drums and are then cross-linked by radiation in a separate operation and are subsequently tested by means of compressed air while they are backwound in the final lengths of 120 to 200 meters or more after such backwinding. In that operation it is not possible, for technical reasons, to use externally grounded metal probes which are held from the outside in a fixed position inside the profile or section.

For this reason it is an object of the invention to provide apparatus which can be used for an economical testing of plastic profiles or sections, particularly plastic tubes which have been cross-linked by radiation, in order to detect defects in the tube wall, particularly punctures, in a process which can be automated; that apparatus should reliably avoid the disadvantages of the previously known apparatus and processes for testing plastic profiles or sections.

This is accomplished in accordance with the invention in that the moving plastic tube is surrounded by a first electrode and by a second electrode, which is properly spaced from the first, one electrode is connected to a voltage source, the other electrode is grounded and is insulated from the first electrode, and a probe is disposed inside the plastic tube and extends herein at least from the beginning of the first electrode to the end of the second electrode and is secured by means of an insulator to a floating element, which is held in position by a magnet surrounding the sliding tubing.

The electrodes consist desirably of fine metal fibers, which are in sliding contact with the surface of the plastic profile or section to be tested and which surround the cross-section of said profile or section without interruption.

The electrodes consist desirably of closely fitting metal cylinders.

The electrodes consist desirably of blades or other electrically conductive materials, which surround and closely fit the periphery of the profile or section.

The probe disposed inside the tubing desirably consists of an electric braid, which is electrically conductive.

The probe disposed inside the tubing is desirably provided on its surface with bristlelike fibers.

The connection between the internal probe and the magnetically held floating element is desirably provided by an insulator.

The holding magnet may be a permanent magnet.

Alternatively, the holding magnet may be an electromagnet.

There is desirable a probe for monitoring the probe held inside the tube.

The testing apparatus proposed by the invention affords the advantage that the apparatus permits an economical and, if desired, fully automatic detection of defects which exist in the wall of the profile or section to be tested and which could not be reliably detected before, and particularly permits a reliable detection of the locations of holes and punctures.

BRIEF DESCRIPTION OF THE DRAWING

The apparatus proposed by the invention will now be explained more in detail with reference to an illustrative embodiment, which is diagrammatically shown on the drawing.

FIG. 1 shows a plastic profile or section 1, which moves in the direction of the arrow first through a magnetic holding magnet 2, then through a first electrode 3 and through another electrode 4, which is slightly spaced from the first and is connected to the voltage source, not shown, and comprises metal fibers 5 in contact with the surface of the plastic profile or section 1 at the leading end thereof. The electrode 3 is grounded by a lead 6. A floating element 7 is disposed inside the profile or section 1 and is held by the magnet 2, which surrounds the tubing. By means of an insulator 8 the floating element holds a metal probe 9, which extends at least throughout the length of the two electrodes 3 and 4 and the space between them. The metal probe 9 is preferably made from an electrically conductive, elastic metal braid so that it can adapt itself to surface irregularities and different diameters of the profile or section 1.

Another probe 10 is provided for monitoring the metal probe 9 held inside the profile or section. Any movement of the floating element 7 from its position, for any reason whatever, so that the metal probe 9 is removed from the vicinity of the two cylinders 3 and 4, will be indicated by the monitoring probe 10.

Means which are not shown include an indicating or sequential device and are operated in case of a defect breakdown.

The invention is based on the assumption that the second potential required inside the profile or section 1 for the high voltage measurement can be provided by a "capacitor". Because the probe 9 cannot be held directly from the outside, it is held in known manner by a magnetically attractable floating element 7, which is disposed in the field of a magnet 2, which surrounds the profile or section.

To permit the development of a sufficiently high potential, the cylinder 3 must have an adequately large surface and an appropriate length. The air gap between the inside surface of the cylinder 4 and the outside surface of the plastic profile or section 1 should be as small as possible. The high-voltage source may consist of commercially available high-voltage generators.

It has been found that the following dimensions, which are stated by way of example, will ensure a proper operation of the apparatus proposed by the invention. The voltage source consists of an a.c. voltage generator of 25,000 volts. The electrode 4 has a length of about 30 cm and the electrode 3 a length of about 50 cm. The air gap between the two electrodes is about 20 cm. The probe 9 has a length of about 100 cm. The profile or section 1 consists of a tube having an outside diameter of 18 mm and a wall thichness of 2 and is made of polyethylene cross-linked by radiation.

When the plastic profile or section 1 is moving through the apparatus in the direction of the arrow and the voltage source is operated, an electric field over the probe 9 will build up between the mutually insulated electrodes 3 and 4.

If a defect consisting, e.g., of an electron puncture in the wall of the plastic profile or section 1 appears in the region of the electrodes, there will be a breakdown from the electrodes 3, 4 to the probe 9. That breakdown will initiate the operation of a marking or other switching device by which the defect is recorded and marked so that the defective portion can subsequently be cut off or marked as a reject. Additional control signals may be used, e.g., to shut down the backwinding plant and to produce other effects.

It will be understood that the apparatus proposed by the invention is not restricted to the illustrative embodiment shown on the drawings but may be used to advantage in other fields in which similar problems arise.

I claim:

1. Apparatus for testing plastic tubes for faults characterized in that a moving plastic tube (1) is surrounded by a first electrode and by a second electrode, which is properly spaced from the first, one electrode is connected to a voltage source, the other electrode is grounded and is insulated from the first electrode, and a probe (9) is disposed inside the plastic tube (1) and extends therein at least from the beginning of the first electrode to the end of the second electrode and is secured by means of an insulator to a floating element, which is held in position by a magnet surrounding the moving plastic tube, said probe cooperating with said electrodes to generate an electric field which changes in the presence of a tube fault.

2. Apparatus according to claim 1, characterized in that the probe (9) disposed in the tube (1) consists of an elastic metal braid, which is electrically conductive.

3. Apparatus according to claim 1, characterized in that the probe (9) disposed inside the tube consists of electrically conductive blades.

4. Apparatus according to claim 1, characterized in that the probe (9) disposed inside the tube consists of electrically conductive bristles (5).

5. Apparatus according to any one of claims 1 to 4, characterized in that the electrodes (3, 4) consist of metal tubes which surround and closely fit the plastic tube.

6. Apparatus according to any one of claims 1 to 4, characterized in that the electrodes (3 and 4) consist of bristles, blades or other flexible elements (5), which are electrically conductive and surround the plastic tube as continuously as possible.

7. Apparatus according to claim 1, characterized in that the holding magnet (2) is a permanent magnet.

8. Apparatus according to claim 1, characterized in that the holding magnet (2) is an electromagnet.

9. Apparatus according to claim 1, characterized in that the internal probe (9) and the magnetically held floating element (7) are connected by an insulator (8).

10. Apparatus according to claim 1, characterized in that a probe (10) is provided for monitoring the probe (9) held inside the tube.

* * * * *

UNITED STATES PATENT AND TRADEMARK OFFICE
CERTIFICATE OF CORRECTION

PATENT NO. : 4,590,420
DATED : May 20, 1986
INVENTOR(S) : F. H. Neueder

It is certified that error appears in the above-identified patent and that said Letters Patent is hereby corrected as shown below:

Column 1, line 50 after "material" change "amy" to --may--.

Column 2, line 41, after "an" change "electric" to --elastic--.

Column 3, line 49, change "thichness" to --thickness--.

Column 3, line 49, delete "2" and substitute therefore --2mm--.

Signed and Sealed this

Thirtieth Day of September 1986

[SEAL]

Attest:

DONALD J. QUIGG

Attesting Officer

Commissioner of Patents and Trademarks